Figure 1:
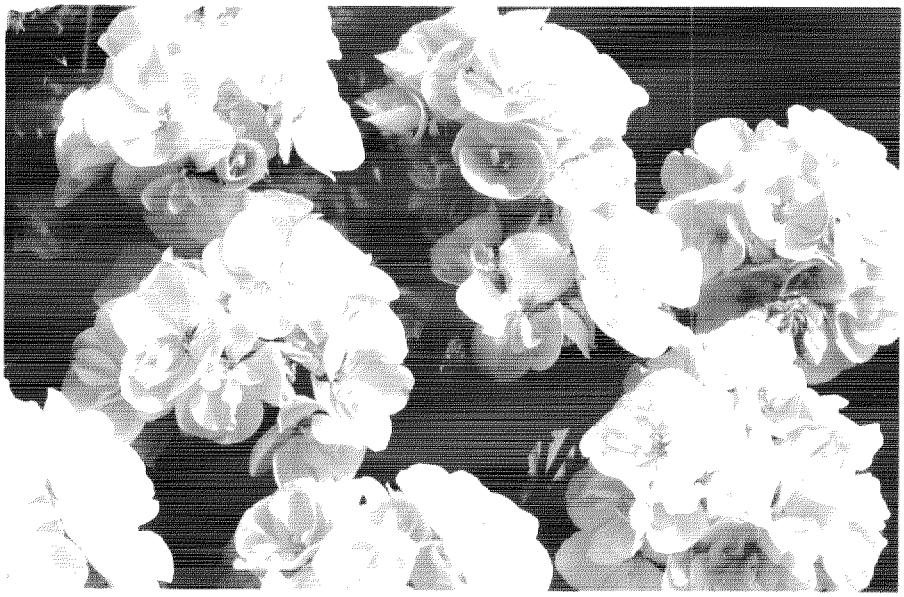

US00PP10349P

United States Patent [19]

Hanes

[11] Patent Number: Plant 10,349

[45] Date of Patent: Apr. 21, 1998

[54] GERANIUM NAMED 'CLIPS LIGHT LAV'

[75] Inventor: Mitchell Eugene Hanes, Morgan Hill, Calif.

[73] Assignee: Goldsmith Seeds, Inc., Gilroy, Calif.

[21] Appl. No.: 748,266

[22] Filed: Nov. 13, 1996

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 9,231 8/1995 Trees ..... Plt./87.12

*Primary Examiner*—James R. Feyrer

*Attorney, Agent, or Firm*—Rothwell, Figg, Ernst & Kurz, pc

[57] ABSTRACT

A new geranium cultivar particularly distinguished by dark green foliage, light bluish pink flower color, and semi-double flowers on large umbels, fast rooting and a vigorous growth habit.

1 Drawing Sheet

BACKGROUND OF THE NEW PLANT

The present invention comprises a new and distinct cultivar of geranium, botanically known as *Pelargonium hortorum* Bailey, and hereinafter referred to by the cultivar name 'Clips Light Lav'. The new cultivar is propagated from a seedling resulting from the cross of a seed parent 3358-1 and the pollen parent known as 3500-2.

'Clips Light Lav' is a product of a planned breeding program intended to create new geranium cultivars with lavender colored flowers, semi-double flower form, dark green foliage, vigorous growth and superior cutting productivity.

The new cultivar was created in 1993 in Gilroy, Calif., and has been repeatedly asexually reproduced by cuttings in Gilory, Calif. and Guatemala over a three year period. It has also been trialed at Okemos, Mich. It has been found to retain its distinctive characteristics through successive propagations; and this novelty appears to be firmly fixed.

DESCRIPTION OF PHOTOGRAPH

This new geranium plant is illustrated by the accompanying photograph which shows blooms, buds, and foliage of the plant in full color, the colors shown being as true as can be reasonably obtained by conventional photographic procedures.

FIG. 1 shows overall plant habit;

DESCRIPTION OF THE NEW CULTIVAR

The following detailed descriptions set forth the distinctive characteristics of 'Clips Light Lav'. The data which defines these characteristics were collected from asexual reproductions carried out by Goldsmith Seeds, Inc. in Gilroy, Calif. The plant history was taken on 20 week old plants, blossomed under natural light in a greenhouse and color readings were taken in the greenhouse (in Gilroy, Calif.) on Jul. 24, 1996 at 2:00 p.m. under ambient light. Color references are primarily to the R.H.S. Colour Chart of The Royal Horticultural Society of London (R.H.S.).

The Plant

Classification:

*Botanical.*—*Pelargonium hortorum* Bailey.

*Commercial.*—Zonal geranium.

Form: Upright compact plant.

Height: 12 to 17 cm, as a 4½ inch pot plant, excluding blooms.

Strength: Good shipping ability as rooted or unrooted cuttings.

Foliage: Abundant quantity.

*Leaves.*—Size: Diameter about 6.4 cm. Shape: Rounded cordate with occasional upfolding between veins. Margin: Irregularly crenate. Texture: Leathery and pubescent on both surfaces, especially along veins. Ribs and veins: Distinctly palmate, 3.6 to 4.0 cm long. Color: Upper side: Dark Green. Underside: Dark Green color. Ribs and veins not prominently different from upper surface. Petioles: About 4.5 to 5.4 cm in length.

The Bud

Size:

*Diameter.*—About 4 mm.

*Length.*—About 11 cm to 12 cm at time of bud opening.

Shape: Pointed ovoid.

Color: Petals when sepals first divide is 73A-B, R.H.S.

Sepals: Primary 5 sometimes 6 in number, flat behind petals. Pointed linear lanceolate, 144A R.H.S. in an open flower.

The Flower

Blooming habit; Continuous throughout the year.

Size: Approximately 4.8–5.0 cm diameter, 2 cm deep, irregularly radially symmetrical.

Form: Cup-shaped when bloom first opens, later flattening to shallow cup shape with maturity.

Petals: 5 imbricate outer petals, 2.2–2.4 cm wide and approximately 2.4 cm long. Three to six inner smaller petaloids of varying shape. Both the outer petals and inner petaloids are light bluish pink, 73C R.H.S. The two upper petals are 73C R.H.S. on the top region but are white from the center of the petal to the base. Color changing little with age. Underside of petals is a blush white with pink margins. Petals and petaloids soft and satiny.

Pedicel: Approximately 2.4–3.0 cm in length

Persistence: Non-shattering flower.

Inflorescence

Type: An umbel composed of approximately 23 flowers, erect or laterally ascending.

Peduncle: Approximately 9–10 cm in length, mostly green with a reddish tint on the side facing the sunlight.

Reproductive Organs

Stamens:

*Anthers.*—8–10 positioned below the mature stigma, dull red prior to anthesis.

*Filaments.*—White.

*Pollen.*—Orange in color.

Pistil:

*Number.*—1.

*Length.*—Approximately 4 mm.

*Stigma.*—5 linear lobes of near equal length, curling back toward ovary, white with a purplish tint.

*Style.*—Length: About 3 mm. Color: White.

*Ovaries.*—At anthesis, densely pubescent with white hairs, oblong. Green drying to a light brown at maturity.

*Fruit.*—Partially fertile.

I claim:

1. A new and distinct cultivar of geranium plant, substantially as herein shown and described, named 'Clips Light Lav', that is characterized by: dark green foliage, light bluish pink flower color, and semi-double flowers on large umbels, fast rooting and a vigorous growth habit.

* * * * *